United States Patent
Lee et al.

(10) Patent No.: US 10,060,859 B2
(45) Date of Patent: Aug. 28, 2018

(54) METHOD OF INSPECTING FOREIGN SUBSTANCE ON SUBSTRATE

(71) Applicant: KOH YOUNG TECHNOLOGY INC., Seoul (KR)

(72) Inventors: Hyun-Seok Lee, Suwon-si (KR); Jae-Sik Yang, Incheon (KR); Ja-Geun Kim, Seoul (KR); Hee-Tae Kim, Yongin-si (KR); Hee-Wook You, Anyang-si (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 65 days.

(21) Appl. No.: 14/781,953

(22) PCT Filed: Apr. 1, 2014

(86) PCT No.: PCT/KR2014/002784
§ 371 (c)(1),
(2) Date: Oct. 2, 2015

(87) PCT Pub. No.: WO2014/163375
PCT Pub. Date: Oct. 9, 2014

(65) Prior Publication Data
US 2016/0025649 A1     Jan. 28, 2016

(30) Foreign Application Priority Data

Apr. 2, 2013    (KR) ........................ 10-2013-0036076
Mar. 20, 2014    (KR) ........................ 10-2014-0032676

(51) Int. Cl.
*G06K 9/00*      (2006.01)
*G01N 21/94*      (2006.01)
(Continued)

(52) U.S. Cl.
CPC ......... *G01N 21/94* (2013.01); *G01N 21/8806* (2013.01); *G06T 7/001* (2013.01);
(Continued)

(58) Field of Classification Search
CPC ... G01N 2021/8864; G01N 2021/8887; G01N 2021/95676; G01N 2021/95638;
(Continued)

(56) References Cited

U.S. PATENT DOCUMENTS 5,717,485 A *   2/1998   Ito .......................... G01N 21/94
                                                                                       356/237.1
7,039,228 B1 *   5/2006   Pattikonda ......... G01B 11/0608
                                                                                    348/87
(Continued)

FOREIGN PATENT DOCUMENTS

| JP | 5-322788 | 12/1993 |
|---|---|---|
| JP | 10-150299 | 6/1998 |

(Continued)

OTHER PUBLICATIONS

International Search Report for International Application No. PCT/KR2014/002784, dated Jul. 22, 2014.

*Primary Examiner* — Aaron W Carter
(74) *Attorney, Agent, or Firm* — Kile Park Reed & Houtteman PLLC

(57) ABSTRACT

In order to inspect a substrate, an image information of a substrate before applying solder is displayed. Then, at least one inspection region on the substrate is image-captured to obtain an image of the inspection region that is image-captured. Then, image information that is to be displayed is renewed and the renewed image information is displayed. And, in order to inspect a foreign substance, obtained image of the inspection region is compared with a reference image of the substrate. Therefore, an operator can easily catch a (Continued)

region corresponding to a specific region of the image that is displayed, and easily detect a foreign substance on the substrate.

12 Claims, 13 Drawing Sheets

(51) Int. Cl.
  *G01N 21/88* (2006.01)
  *G06T 7/00* (2017.01)
  *G06T 11/60* (2006.01)
  *G01N 21/956* (2006.01)
(52) U.S. Cl.
  CPC ...... *G06T 11/60* (2013.01); *G01N 2021/8845* (2013.01); *G01N 2021/95638* (2013.01); *G01N 2201/061* (2013.01); *G01N 2201/13* (2013.01); *G06T 2207/10004* (2013.01); *G06T 2207/10024* (2013.01); *G06T 2207/30141* (2013.01)
(58) Field of Classification Search
  CPC .......... G01N 2021/95646; G01N 2021/95653; G01N 21/88; G01N 21/8851; G01N 21/956; G01N 2223/611; G01N 2223/6113; G01N 2291/2697; G06T 7/0002; G06T 7/001; G06T 7/0014; G06T 7/20; G06T 7/0016; G06T 2207/30108; G06T 2207/30141; G03F 7/7065; G03F 7/70666; G03F 7/70616; G03F 1/0092; G01B 9/04
  See application file for complete search history.

(56) References Cited

U.S. PATENT DOCUMENTS

| | | | |
|---|---|---|---|
| 7,181,058 B2 * | 2/2007 | Weisgerber | H05K 13/08 250/559.34 |
| 2002/0088952 A1 | 7/2002 | Rao et al. | |
| 2003/0169418 A1 * | 9/2003 | Fujii | G01N 21/8806 356/237.2 |
| 2006/0017676 A1 | 1/2006 | Bowers et al. | |
| 2007/0263920 A1 * | 11/2007 | Fujii | G01N 15/1463 382/141 |
| 2010/0290696 A1 | 11/2010 | Jeong et al. | |
| 2010/0295941 A1 | 11/2010 | Jeong et al. | |
| 2011/0002527 A1 | 1/2011 | Jeong et al. | |
| 2011/0051130 A1 * | 3/2011 | Kawahara | G01N 21/94 356/237.3 |
| 2011/0191050 A1 * | 8/2011 | Jeong | G06F 19/00 702/82 |
| 2011/0255771 A1 | 10/2011 | Kwon | |
| 2012/0128232 A1 * | 5/2012 | Jeong | G01B 11/25 382/149 |
| 2014/0029788 A1 * | 1/2014 | Kang | G06K 9/0051 382/103 |
| 2016/0025649 A1 * | 1/2016 | Lee | G06T 11/60 382/147 |
| 2017/0032531 A1 * | 2/2017 | Nagata | G01B 11/2513 |

FOREIGN PATENT DOCUMENTS

| | | |
|---|---|---|
| JP | 2000-124598 | 4/2000 |
| JP | 2002-42112 | 2/2002 |
| JP | 2003-110299 | 4/2003 |
| JP | 2003-141509 | 5/2003 |
| JP | 2004-125434 | 4/2004 |
| JP | 2004-301574 | 10/2004 |
| JP | 2005-164455 | 6/2005 |
| JP | 2006-17474 | 1/2006 |
| JP | 2007-10497 | 1/2007 |
| JP | 2008-292430 | 12/2008 |
| JP | 2009-128345 | 6/2009 |
| JP | 2011-123019 | 6/2011 |
| JP | 2012-103225 | 5/2012 |
| JP | 2012-108134 | 6/2012 |
| JP | 2012-117920 | 6/2012 |
| JP | 2012-209085 | 10/2012 |
| KR | 10-2011-0002981 | 1/2011 |
| KR | 10-2011-0089486 | 8/2011 |
| KR | 10-2011-0115059 | 10/2011 |
| WO | 2007/074770 | 7/2007 |

* cited by examiner

METHOD OF INSPECTING FOREIGN SUBSTANCE ON SUBSTRATE

TECHNICAL FIELD

The present invention relate to a method of inspecting a foreign substance on a substrate. More particularly, the present invention relate to a method of inspecting a foreign substance on a substrate, which is performed during inspecting a substrate.

BACKGROUND ART

In general, an electronic apparatus includes at least one printed circuit board (PCB), and a circuit pattern, a connection pad and various circuit devices such as a driving chip electrically connected to the connection pad, etc. are mounted on the PCB. In order to inspect whether the various circuit devices are properly mounted or disposed on the PCB, a shape measuring apparatus may be used.

A conventional shape measuring apparatus displays an image of a substrate on a monitor screen in order that an operator performs a serial inspection. In this case, a pad region where a solder is applied, is displayed by using a gerber data.

However, the image of a substrate displays only a portion such as a pad region but not a stencil, a hole, etc. unlikely real image. Therefore, an operator may have a problem of inspecting a desired region, which is induced by a difference between a real image and a displayed image in performing the serial inspection.

For example, catching a real position with a problem on a substrate through a displayed image of a substrate may be hard and require too much time.

Therefore, a method of displaying, through which a real position corresponding to a specific region of a displayed substrate image can be easily caught, is required.

On the other hand, it is very difficult to detect a foreign substance on a substrate, since a substrate image displayed in order to perform a serial inspection is not a real image of substrate.

This substance may include a malfunction of a substrate. Therefore, a method of inspecting a foreign substance on a substrate, through which the substance can be detected, is required.

DISCLOSURE

Technical Problem

Therefore, the technical problem of the present invention is to provide a method of inspecting a foreign substance on a substrate, through which a foreign substance can be easily and exactly detected.

Technical Solution

A method of inspecting a foreign substance on a substrate according to an embodiment of the present invention, includes obtaining 3-dimensional information based on height of a substrate by using at least one grid pattern light, detecting a foreign substance of the substrate by using the 3-dimensional information based on height, obtaining 2-dimensional information of the substrate per color by using a plurality of color light, detecting a foreign substance of the substrate by using the 2-dimensional information per color, and merging a detection result of a foreign substance, performed by using the 3-dimensional information based on height and a detection result of a foreign substance, performed by using the 2-dimensional information per color.

For example, detecting a foreign substance of the substrate by using the 2-dimensional information per color, may include obtaining master images of a master substrate per color by using the plurality of color light, obtaining images of the substrate per color by using the plurality of color light, and comparing the master images per color and the images per color to detect a foreign substance.

Comparing the master images per color and the images per color to detect a foreign substance, may include merging the images of the substrate per color to generate a substrate image, merging the master images of the master substrate per color to generate a master substrate image, and comparing difference of the substrate image and the master substrate image to detect a foreign substance.

Comparing the master images per color and the images per color to detect a foreign substance, may include forming a chroma map of the substrate by using the images of the substrate per color, forming a chroma map of the master substrate by using the master images of the master substrate per color, and comparing the chroma map of the substrate and the chroma map of the master substrate to detect a foreign substance.

For example, merging a detection result of a foreign substance, performed by using the 3-dimensional information based on height and a detection result of a foreign substance, performed by using the 2-dimensional information per color, may include determining a foreign substance as a final foreign substance, when the foreign substance is considered as a foreign substance in both of inspection by using the 3-dimensional information based on height and inspection by using the 2-dimensional information per color.

Before detecting a foreign substance of the substrate by using the 3-dimensional information based on height and detecting a foreign substance of the substrate by using the 2-dimensional information per color, the method may further include obtaining a mask information regarding to the substrate by using a infrared lighting, and excluding wrongly inspectable material from an inspection target to be detected by forming a mask based on the mask information. For example, the mask information may include a hole information formed at the substrate.

A method of inspecting a foreign substance on a substrate according to another exemplary embodiment of the present invention, includes obtaining master images of a master substrate per color by using a plurality of color light, obtaining images of a substrate per color by using the plurality of color light, forming a master substrate image by merging the master images of the master substrate per color and a substrate image by merging the images of the substrate per color, detecting a first foreign substance by comparing the substrate image and the master substrate image, forming a chroma map of the master substrate by using the master images of the master substrate per color and a chroma map of the substrate by using the images of the substrate per color, detecting a second foreign substance by comparing the chroma map of the substrate and the chroma map of the master substrate, and merging a detection result of the first foreign substance and a detection result of the second foreign substance.

For example, merging a detection result of the first foreign substance and a detection result of the second foreign substance, may include determining a foreign substance as a final foreign substance, when the foreign substance is considered as a foreign substance in at least one of a detection result of the first foreign substance and a detection result of the second foreign substance.

Before detecting a first foreign substance and a second foreign substance, the method may further include obtaining a mask information regarding the substrate, and excluding wrongly inspectable material from an inspection target to be detected by forming a mask based on the mask information. For example, excluding wrongly inspectable material from an inspection target to be detected by forming a mask based on the mask information, may include forming a hole mask such that a hole formed at the substrate is included, forming an edge mask such that a circuit pattern formed on the substrate is included, and excluding the hole mask and the edge mask from the inspection target to be detected.

For example, the method may further include obtaining 3-dimensional information based on height of a substrate by using at least one grid pattern light, detecting a foreign substance of the substrate by using the 3-dimensional information based on height, and merging a detection result based on the 3-dimensional information based on height and a detection result based on 2-dimensional information of color, after detecting a foreign substance of the substrate by using the 3-dimensional information based on height and merging a detection result of the first foreign substance and a detection result of the second foreign substance. Merging a detection result based on the 3-dimensional information based on height and a detection result based on 2-dimensional information of color, may include determining a foreign substance as a final foreign substance, when the foreign substance is considered as a foreign substance in both of the detection result based on the 3-dimensional information based on height and the detection result based on 2-dimensional information of color.

A method of inspecting a foreign substance on a substrate according to still another exemplary embodiment of the present invention, includes displaying an image information of a substrate before applying solder, image-capturing at least one inspection region on the substrate to obtain an image of the inspection region that is image-captured, renewing the image information that is displayed with the image of the inspection region that is obtained to display a renewed image, and comparing the image of the inspection region and a reference image of the substrate to inspect a foreign substance.

For example, the image information in a step of displaying an image information of a substrate before applying solder, may include a gerber information, and the gerber information is a black-and-white image information, and the image information that is renewed in a step of renewing the image information that is displayed with the image of the inspection region that is obtained to display a renewed image, is a color image information.

For example, image-capturing at least one inspection region on the substrate to obtain an image of the inspection region that is image-captured, may include at least one of emitting a grid pattern light onto the inspection region of the substrate, and emitting at least one color light onto the inspection region of the substrate for image-capturing.

For example, the method may further include obtaining a reference image of the substrate before displaying an image information of a substrate before applying solder, and the reference image includes at least one of an image obtained by emitting at least one color light onto the inspection region of a previously selected reference substrate, and an image obtained by emitting at least one grid pattern light onto the inspection region of the reference substrate.

Advantageous Effects

According to the present invention described above, the image of the substrate, which is displayed for performing inspection, is renewed to be captured inspection region image so that an operator can easily catch a real portion in the real substrate, which corresponds to a portion in the displayed image.

Additionally, a foreign substance can be easily detected by comparing the obtained image of the inspection region with the reference image of the substrate.

Further, when a bright foreign substance and a dark foreign substance are separately detected and merged in inspecting of a foreign substance of a substrate, a reliability of detection of a foreign substance can be improved.

Further, when the detection result obtained by using the 3-dimensional information based on height and the detection result obtained by using 2-dimensional information per color are merged, a reliability of detection of a foreign substance can be improved in detecting a foreign substance of a substrate.

Further, more easy or precise detection can be performed by excluding a region that is unnecessary or may induce error in inspecting a foreign substance by using infrared lighting.

MODE FOR INVENTION

Figure 1:
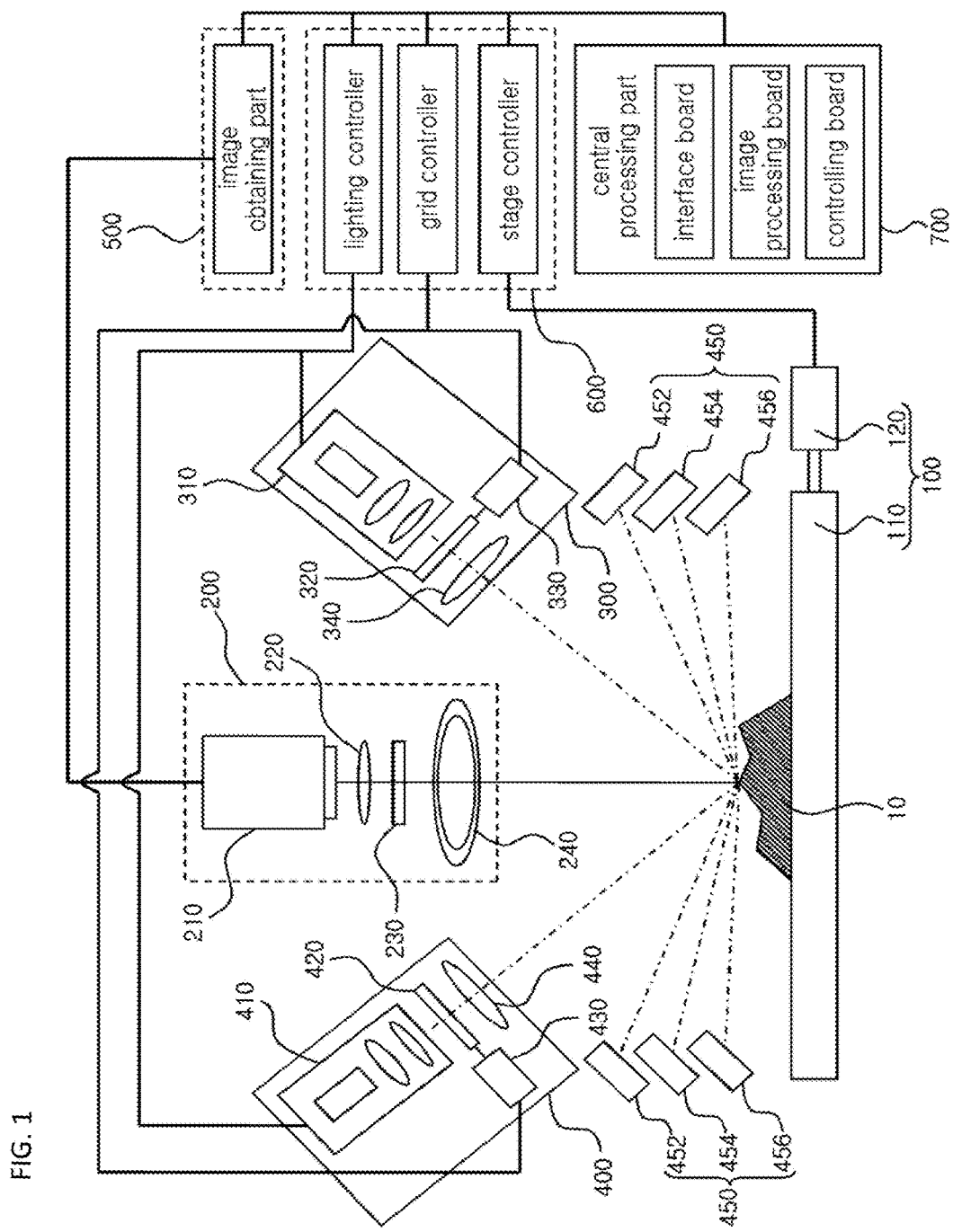
FIG. 1 is a conceptual view showing a 3-dimensional shape measuring apparatus according to an embodiment of the present invention.

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that, although the terms first, second, third etc. may be used herein to describe various elements, components, regions, layers and/or sections, these elements, components, and/or sections should not be limited by these terms. These terms are only used to distinguish one element, component, region, layer or section from another region, layer or section. Thus, a first element, component, or section discussed below could be termed a second element, component, or section without departing from the teachings of the present invention.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

For convenience, same numerals are used for identical or similar elements of an apparatus of cutting a tempered substrate and the conventional one.

Hereinafter, with reference to the drawings, preferred embodiments of the present invention will be described in detail.

FIG. 1 is a conceptual view showing a 3-dimensional shape measuring apparatus according to an embodiment of the present invention.

Referring to FIG. 1, a 3-dimensional shape measuring apparatus, which can be applied to a method of inspecting 3-dimensional image according to an embodiment of the present invention, may include a measurement stage part 100, an image-capturing part 200, a first projecting part 300, a second projecting part 400, a lighting part 450, an image obtaining part 500, a module controlling part 600, and a central processing part 700.

The measurement stage part 100 may include a stage 110 which supports a target object 10 and a stage transfer unit 120 which transfers the stage 110. In the embodiment, measurement position of the target object 100 may be changed as the target object 10 is moved by the stage 110 with respect to the image-capturing part 200 and first and second projecting parts 300 and 400

The image-capturing part 200 is arranged above the stage 110 to capture an image of a target object 10 by receiving a light reflected by the target object 10. In other words, the image-capturing part 200 receives the light which is emitted from the first and second lighting devices 300 and 400 and reflected by the target object 10 and captures the image of the target object.

The image-capturing part 200 may include a camera 210, an image forming lens 220, a filter 230, and a circular lamp 240. The camera 210 receives the light which is reflected by the target object 10 and captures a plane image of the target object 10, in one embodiment, the camera may be a CCD camera or CMOS camera. The image forming lens 220 is arranged at the bottom of the camera 210, receives the light reflected by the target object 10, and forms an image on the camera 210. The filter 230 is arranged at the bottom of the image forming lens 220 to filter the reflected light and provide to the image forming lens 220, in one embodiment, the filter may be one of a frequency filter, a color filter, and a light intensity adjustment filter. The circular lamp 240 is arranged at the bottom of the filter 230 and provides light to capture unusual image such as 2-dimensional image of the target object 10.

The first projecting part 300 may be slantly disposed with respect to the stage 110 supporting the target object 10, for example, at a right side of the image-capturing part 200. The first projecting part 300 may include a first lighting unit 310, a first grid unit 320, a first grid transfer unit 330 and a first condensing lens 340. The first lighting unit 310 includes a lighting source and at least one lens to generate a light, and the first grid unit 320 is arranged at the bottom of the first lighting unit 310 to convert the light emitted from the first lighting unit 310 to a first grid pattern light having grid pattern. The first grid transfer unit 330 is connected to the first grid unit 320 to transfer the first grid unit 320. In one embodiment, a piezoelectric transfer unit or a fine linear transfer unit may be used as the first grid transfer unit 330. The first condensing lens 340 is arranged at the bottom of the first grid unit 320 to condense the first grid pattern light which has passed the first grid unit 320 to the target object 10.

The second projecting part 400 may be slantly disposed with respect to the stage 110 supporting the target object 10, for example, at a left side of the image-capturing part 200. The second projecting part 400 may include a second lighting unit 410, a second grid unit 420, a second grid transfer unit 430 and a second condensing lens 440. The elements of second projecting part 300 are substantially the same as the first projecting part 300, and the same explanations is omitted.

When first projecting part 300 projects N-number of first grid pattern lights onto the target object 10 during the first grid transfer unit 330 moves the first grid unit 320 step by step, the image-capturing part 200 may capture N-number of first pattern images in sequence by receiving the N-number of first grid pattern light reflected by the target object 10. Further, When second projecting part 400 projects N-number of second grid pattern lights onto the target object 10 during the second grid transfer unit 430 moves the first grid unit 420 step by step, the image-capturing part 200 may capture N-number of second pattern images in sequence by receiving the N-number of second grid pattern light reflected by the target object 10. The 'N' described above is an integer. For example, the 'N' may be three or four.

In the present embodiment, only the first and second projecting parts 300 and 400 emit the first and second grid pattern lights respectively, but the number of the projecting part may be equal to or greater than three. That is, the grid pattern light may be emitted toward the target object 10 in various directions to get various pattern images. For example, when three projecting parts are arranged to form a triangle, three grid pattern lights may be emitted onto the target object 10 in different directions, and when four projecting parts are arranged to form a square, four grid pattern lights may be emitted onto the target object 10 in different directions. Further, the number of the projecting parts may be eight. In this case, images can be captured by emitting grid pattern light in eight directions.

The lighting part 450 irradiates a light toward the target object 10 to capture 2-dimensional image of the target object 10. In one embodiment, the lighting part 450 may include a red lighting 452, a green lighting 454, and a blue lighting 456. For example, the red lighting 452, the green lighting 454 and the blue lighting 456 may be arranged above the target object in circular to irradiate each of red, green, and blue lights toward the target object 10, or may be arranged with different heights as shown in FIG. 1.

The image obtaining part 500 is electrically connected to the camera 210 of the image-capturing part 200 to obtain and store pattern images generated by using the first and second projecting parts 300 and 400 from the camera 210. Also, the image obtaining part 500 obtains and stores 2-dimensional images generated by using the lighting part 450 from the camera 210. For example, the image obtaining part 500 includes an imaging system which receives and stores N-number of first pattern images and N-number of second pattern images captured by the camera 210.

The module controlling part 600 is electrically connected to the measurement stage part 100, the image-capturing part 200, the first projecting part 300 and second projecting part 400 to control them. For example, the module controlling part 600 includes a lighting controller, a grid controller, and a stage controller. The lighting controller controls the first and second lighting units 310 and 410 and to generate lights, the grid controller controls the first and second grid transfer units 330 and 430 to move the first and second grid units 320 and 420. The stage controller controls the stage transfer unit 120 to move the stage 110 to up down left right side.

The central processing part 700 is electrically connected to the image obtaining part 500 and the module controlling part 600 to control them. In more detail, the central processing part 700 may measure 3-dimensional shape of the target object 110 by receiving and processing the N-number of first pattern images and N-number of second pattern images from the imaging system of the image obtaining part 500. Also, the central processing part 700 may control each of the light controller, the grid controller, and the state controller. In order for that, the central processing part 700 may include an image processing board, a controlling board, and an interface board.

Hereinafter, a method of inspecting a substrate with a target object 10, and a method of inspecting a foreign substance on a substrate by using the 3-dimensional shape measuring apparatus described above, will be explained referring to figures.

Figure 2:
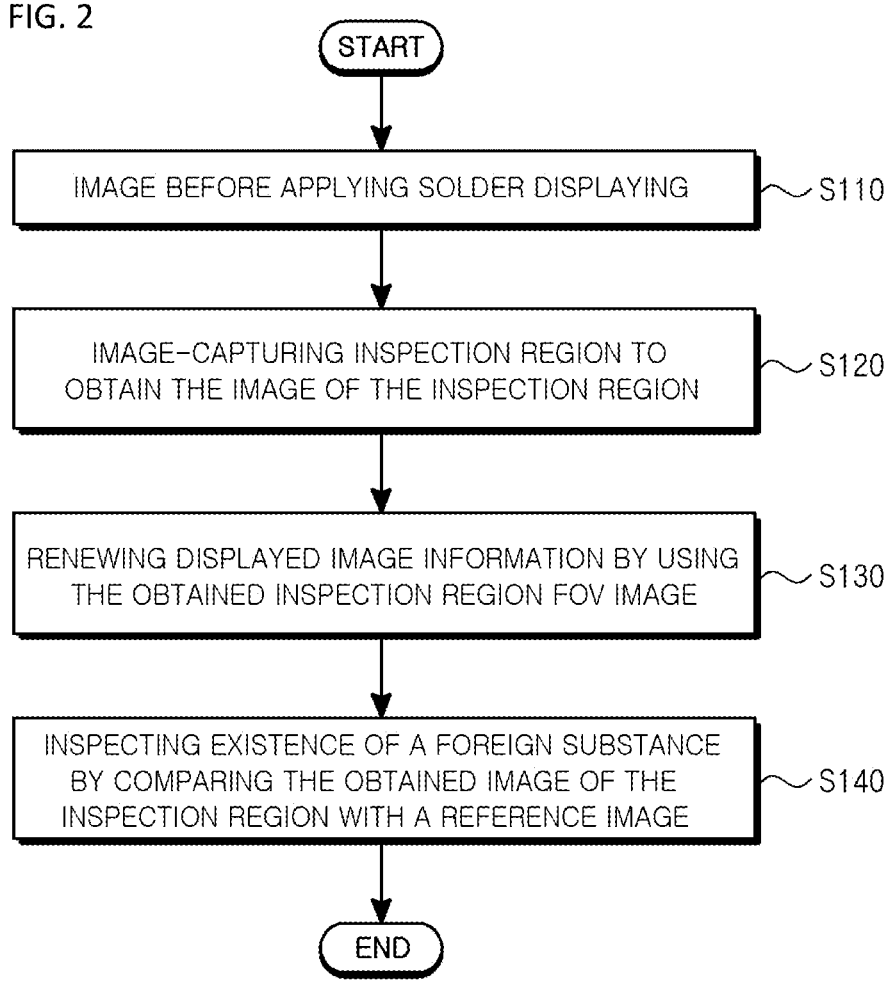
FIG. 2 is a flow chart showing a method of inspecting a substrate and a method of inspecting a foreign substance on a substrate according to an embodiment of the present invention.
Figure 3:
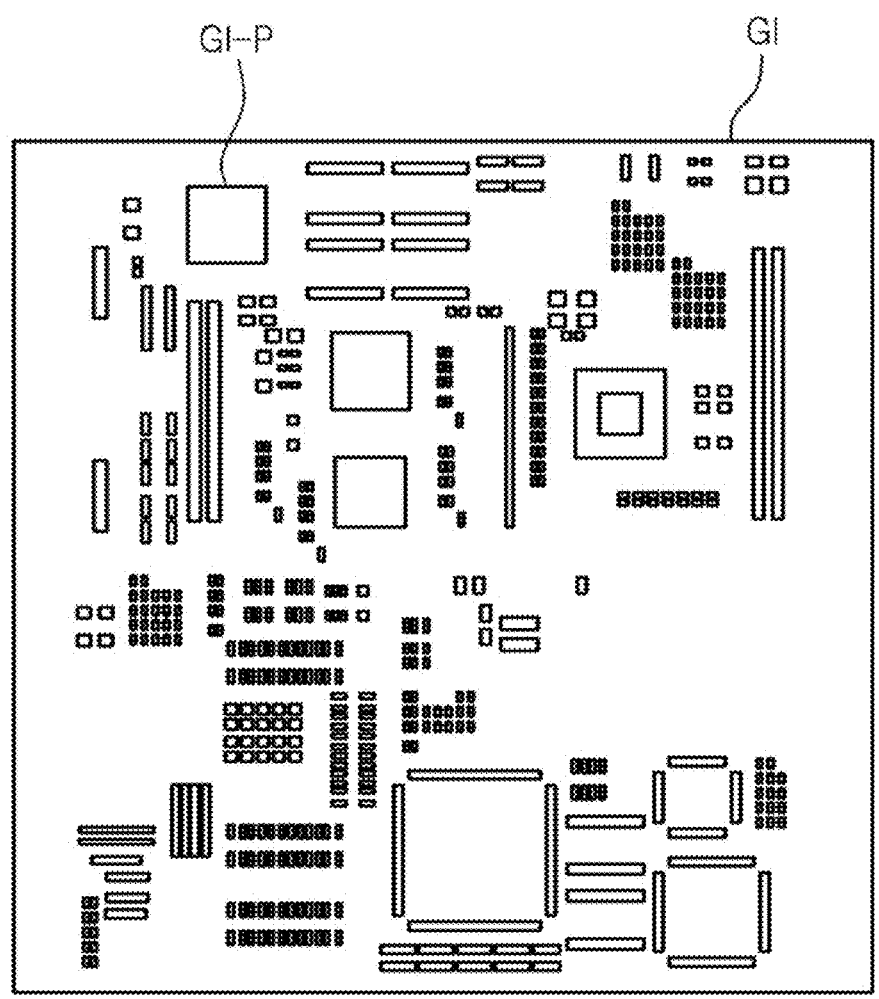
FIG. 3 is a plan view showing an example of image information of a substrate displayed through a step of displaying image information of a substrate in FIG. 2.
Figure 4:
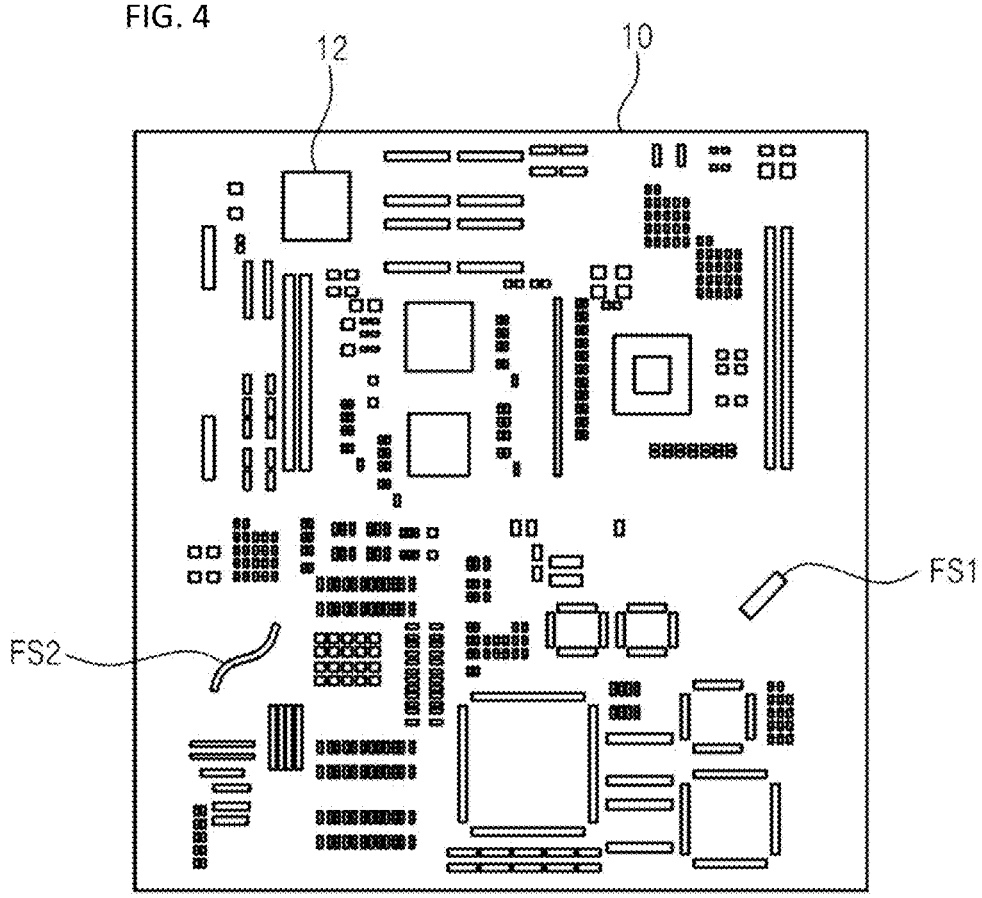
FIG. 4 is a plan view showing a real substrate corresponding to the image of the substrate in FIG. 3.

FIG. 2 is a flow chart showing a method of inspecting a substrate and a method of inspecting a foreign substance on a substrate according to an embodiment of the present invention, FIG. 3 is a plan view showing an example of image information of a substrate displayed through a step of displaying image information of a substrate in FIG. 2, and FIG. 4 is a plan view showing a real substrate corresponding to the image of the substrate in FIG. 3.

Referring to FIG. 2 through FIG. 4, in order to inspect a substrate 10 according to an embodiment of the present invention, an image information of a substrate 10 before applying solder is displayed (S110).

For example, the image information of a substrate 10 may include a gerber information of the substrate 10. The gerber information of the substrate 10 may be an information of a design standard of the substrate 10 before applying solder, and may be displayed on a monitor of an operator as a gerber image GI shown in FIG. 3.

As shown in FIG. 3, the gerber image GI may include pads GI-P with various shapes, on which solder is applied, and the gerber information may be a black-and-white image information.

Then, at least one image of at least one inspection region on the substrate is captured to obtain image of captured inspection region (S120).

The inspection region is a target region to be measured or inspected on the substrate 10, and can be set automatically or by an operator. The substrate 10 may be divided into several regions with definite area to be set as the inspection region, or the whole region of the substrate 10 may be set as the inspection region. For example, the region with definite area may be defined as a field of view (FOV) of the camera 210 of the image-capturing part 200.

Figure 5:
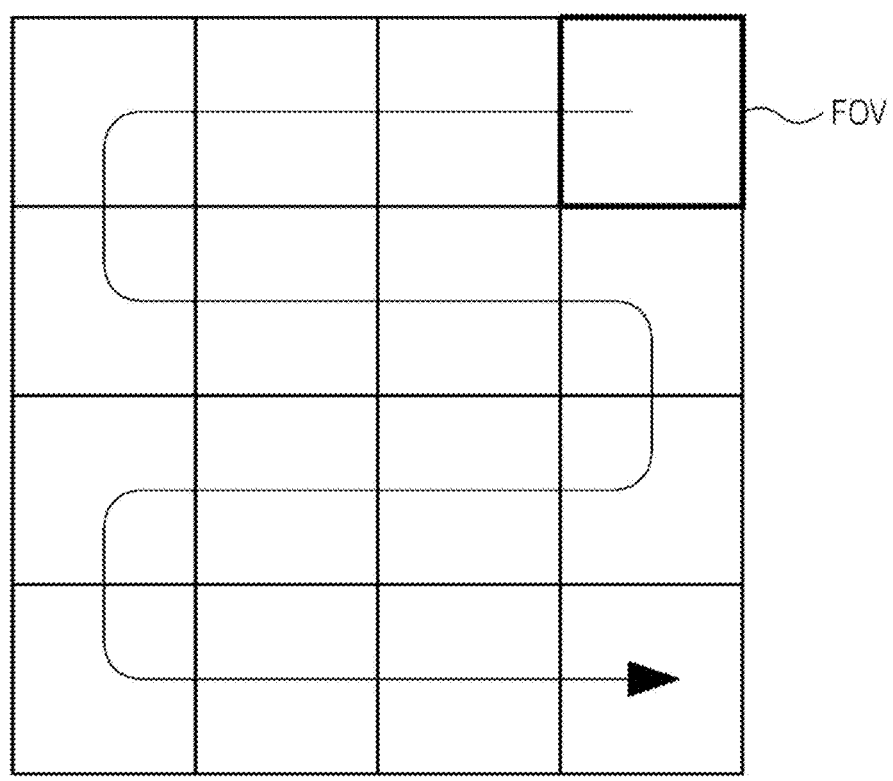
FIG. 5 is a conceptual view showing an example of a step of obtaining an image of an inspection region on a substrate in FIG. 2.

FIG. 5 is a conceptual view showing an example of a step of obtaining an image of an inspection region on a substrate in FIG. 2.

Referring to FIG. 5, the inspection region FOV of the substrate 10 may be defined by the field of view of the camera 210, and may be captured along an arrow direction.

In FIG. 5, all regions of the substrate 10 are image-captured. However, some required regions may be selectively captured.

Image-capturing of the inspection region FOV may be performed, for example, by at least one of the projection parts 300 and 400 and the lighting part 450.

That is, the projecting parts 300 and 400 may emit grid pattern light onto the inspection region FOV, so that the inspection region FOV may be image-captured. In this case, the image of the inspection region FOV includes 3-dimensional image based on height information.

On the other hand, the light part 450 may emit at least one color light onto the inspection region FOV, so that the inspection region FOV may be image-captured. In this case, the image of the inspection region FOV includes 2-dimensional plane image.

Then, displayed image information is renewed by using the obtained inspection region FOV image, and the renewed image information is displayed (S130).

In this case, the renewed image information may be color image information.

The camera 210 providing the renewed image information may be color camera. Alternatively, the camera 210 obtaining the image of the inspection region FOV may be a black-and-white camera. When the image of the inspection region FOV is an image obtained by using the lighting part 450, the renewed image can be converted into a color image since the images obtained by color lights emitted by the lighting part 450 has difference, even though the camera 210 is a black-and-white camera.

Figure 6:
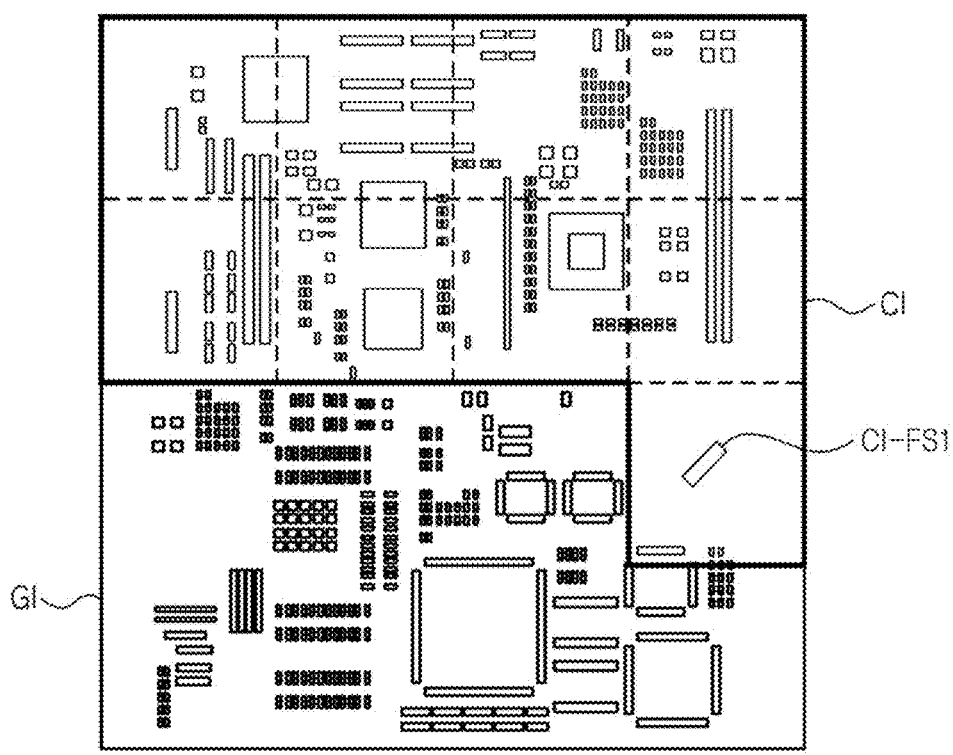
FIG. 6 is a plan view for explaining a process of displaying renewed image information in FIG. 2.

FIG. 6 is a plan view for explaining a process of displaying renewed image information in FIG. 2.

Referring to FIG. 6, the renewed image information corresponds to an internal area of bold line, and image information that is not renewed corresponds to an outer area of the bold line.

The image-captured inspection region as shown in FIG. 5 may be real time renewed as shown in FIG. 6.

As described above, in order to perform inspection, the image of the substrate 10, which is displayed, is renewed as the image of the image-captured inspection region FOV so that an operator can easily match the image of the substrate 10, which is displayed, with a real substrate 10. Further, when the gerber information is black-and-white and the renewed image information is color, the operator can more easily catch the position of the real substrate 10 since the operator uses the renewed color image of the substrate 10, which is displayed.

On the other hand, this step can be omitted in the method of inspecting a foreign substance.

Then, the existence of a foreign substance is inspected by comparing the obtained image of the inspection region FOV with a reference image of the substrate 10 (S140).

For example, the reference image of the substrate 10 can be obtained from a reference substrate that is previously selected. For example, the reference substrate may be a master substrate or a master board. The reference substrate is previously selected, and the inspection region FOV, which is previously explained, is image-captured from the reference substrate as the same way previously explained to get the reference image.

That is, the reference image of the substrate 10 may include an image captured through emitting at least one color light onto the inspection region FOV of the reference substrate by using the light part 450.

In this case, the reference image is 2-dimensional plane image, and the reference image is compared with the captured image of the inspection region FOV so that a different portion may be considered as a foreign substance.

For example, when there exist first and second foreign substances FS1 and FS2 on the substrate 10 as shown in FIG. 4, the reference image does not contain the foreign substances FS1 and FS2 but the captured image CI contains the foreign substances FS1 and FS2 as shown in FIG. 6. Therefore, the different portion CI-FS1 obtained by comparing the reference image and the captured image CI of the inspection region FOV may be considered as a foreign substance.

Further, the reference image of the substrate 10 may further include an image captured through emitting at least one grid pattern light onto the inspection region FOV of the reference substrate by using the projecting parts 300 and 400.

In this case, the reference image is 3-dimensional image based on height, and the reference image is compared with the captured image of the inspection region FOV so that a different portion may be considered as a foreign substance.

For example, when there exist first and second foreign substances FS1 and FS2 on the substrate 10 as shown in FIG. 4, the reference image does not contain the foreign substances FS1 and FS2 but the heights of the foreign substances FS1 and FS2 in the captured image are different from those in the reference image. Therefore, the different portion obtained by comparing the reference image and the captured image CI of the inspection region FOV may be considered as a foreign substance.

Alternatively, in the present step, the foreign substance can be detected by using only the obtained 3-dimensional image of the inspection region FOV based on height instead of inspecting the foreign substance by comparing the obtained 3-dimensional image of the inspection region FOV with the reference image of the substrate 10.

That is, when the image of the inspection region FOV, which is obtained by using the projecting parts 300 and 400, is 3-dimensional image based on height, an abrupt height change or a portion exceeding a previously set value may be considered as a foreign substance.

For example, when the first and second foreign substances FS1 and FS2 are exist on the substrate 10 as shown in FIG. 4, heights of the first and second foreign substances FS1 and FS2 may abruptly increase or exceed a previously set value in the obtained 3-dimensional image based on height. Therefore, the abrupt height change or the portion exceeding a previously set value may be considered as a foreign substance without comparing the reference image with the obtained image.

On the other hand, the reference image can be obtained before the step S110 in which the image information of the substrate 10 is displayed.

According to the present invention described above, the image of the substrate, which is displayed for performing inspection, is renewed to be captured inspection region image so that an operator can easily catch a real portion in the real substrate, which corresponds to a portion in the displayed image.

Additionally, a foreign substance can be easily detected by comparing the obtained image of the inspection region with the reference image of the substrate.

Figure 7:
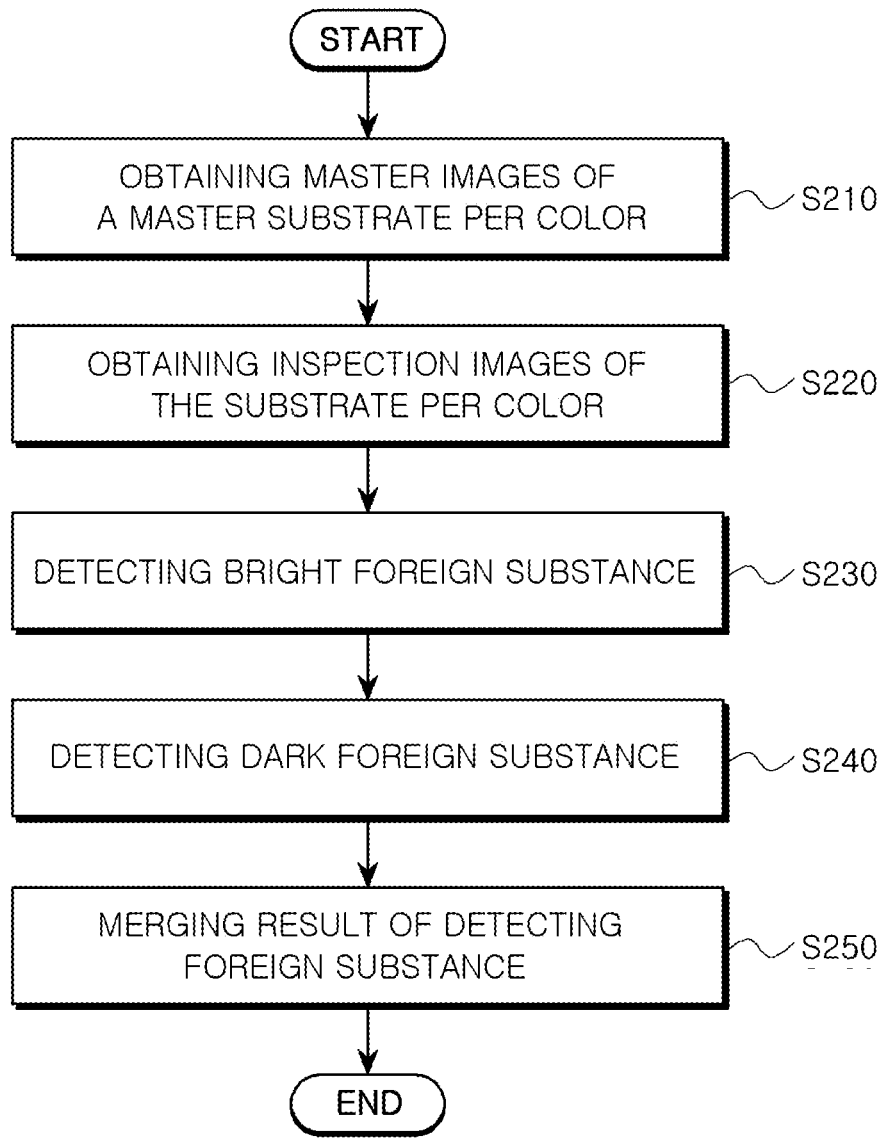
FIG. 7 is a flow chart showing a method of inspecting a foreign substance according to another embodiment of the present invention.

FIG. 7 is a flow chart showing a method of inspecting a foreign substance according to another embodiment of the present invention.

Referring to FIG. 7, in order to inspect a foreign substance on a substrate according to another embodiment of the present invention, master images of a master substrate per color is obtained by using a plurality of color lights (S210).

For example, a red master image of the master substrate is obtained by using a red light emitted by the red lighting 452, a green master image of the master substrate is obtained by using a green light emitted by the green lighting 454, and a blue master image of the master substrate is obtained by using a blue light emitted by the blue lighting 456.

Then, inspection images of the substrate 10 are obtained per color by using the plurality of color lights (S220).

For example, a red inspection image of the substrate 10 is obtained by using a red light emitted by the red lighting 452, a green inspection image of the substrate 10 is obtained by using a green light emitted by the green lighting 454, and a blue inspection image of the substrate 10 is obtained by using a blue light emitted by the blue lighting 452.

Then, a foreign substance is detected by comparing the master images per color and the obtained images per color.

Foreign substances may have various color characteristics. For example, a substance may be characterized by a bright foreign substance and a dark foreign substance.

The bright foreign substance and the dark foreign substance are characterized by relative brightness with respect to the substrate 10. The bright foreign substance and the dark foreign substance may be detected by different method. Therefore, more precise detection may be performed.

Hereinafter, a process for detecting foreign substance according to brightness by comparing the master images per color and the obtained images per color.

First, a bright foreign substance such as dust, chip, etc. is detected by comparing the master images per color and the obtained images per color (S230).

Figure 8:
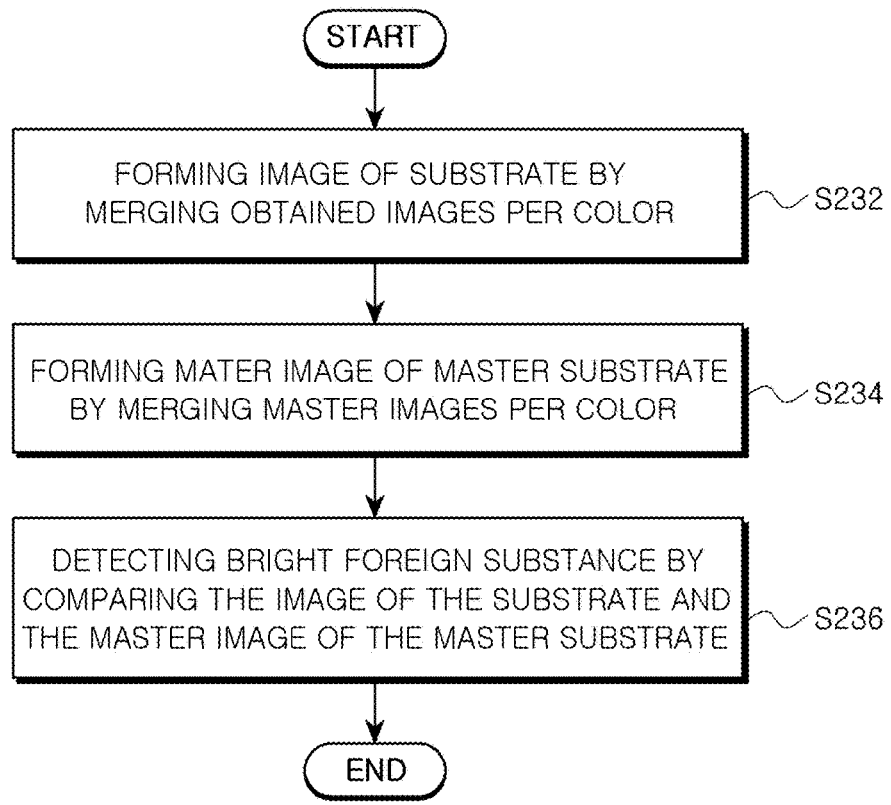
FIG. 8 is a flow chart showing a process of detecting a bright foreign substrate.

FIG. 8 is a flow chart showing a process of detecting a bright foreign substrate.

Referring to FIG. 8, the obtained images per color are merged to form a substrate image regarding the substrate 10 (S232). For example, intensities of each of the red inspection image, the green inspection image and the blue inspection image are merged per pixel to form an image of the substrate.

Aside from forming the images of the substrate, the master images per color are merged to form an image of the master substrate (S234). For example, intensities of each of the red master image, the green master image and the blue master image are merged per pixel to form an image of the master substrate.

After forming the image of the substrate and the master images of the master substrate, a bright foreign substance is detected by comparing the image and the master image (S236).

Figure 9:
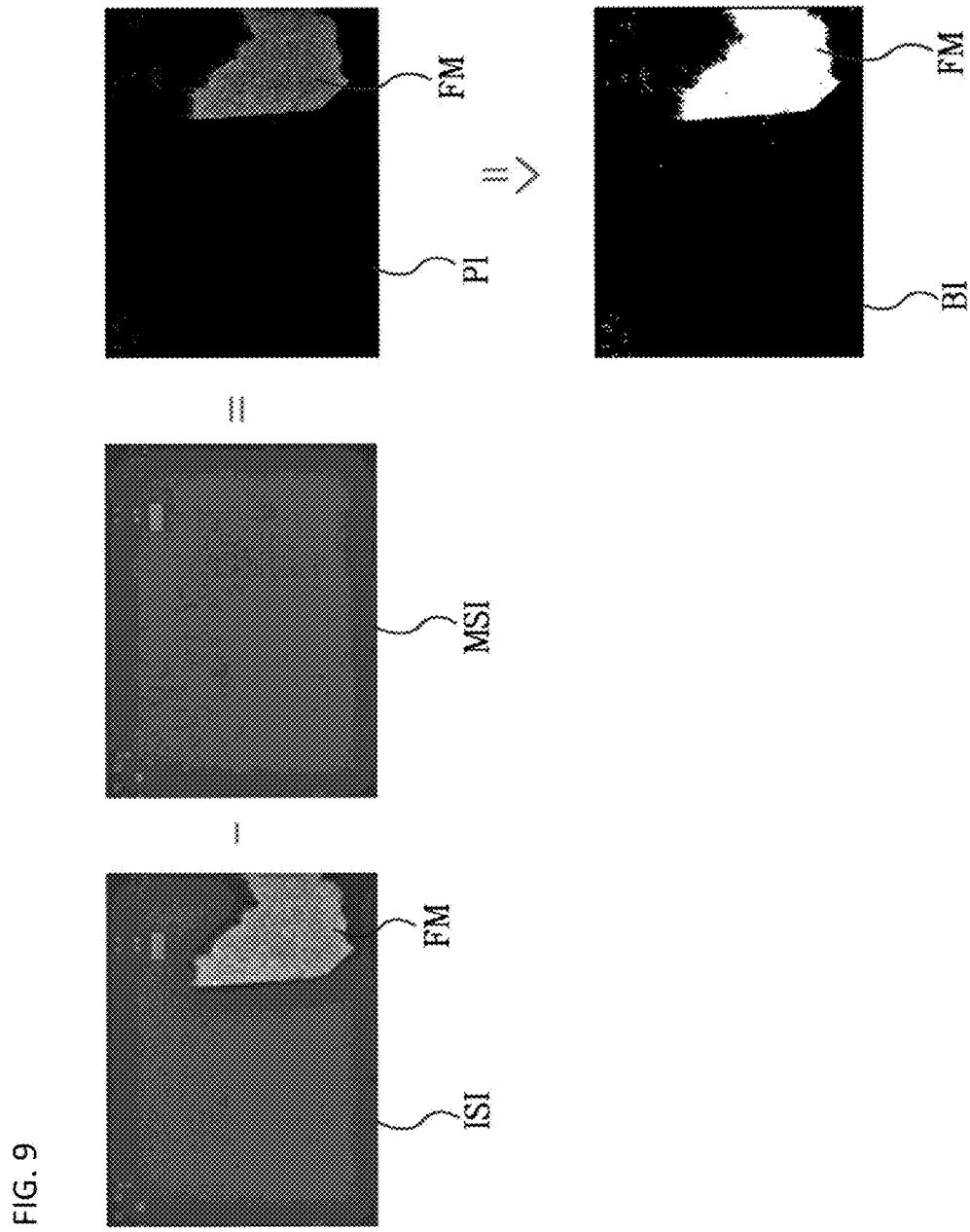
FIG. 9 is a conceptual view showing a process of detecting a bright foreign substance by comparing a substrate image and a master substrate image.

FIG. 9 is a conceptual view showing a process of detecting a bright foreign substance by comparing a substrate image and a master substrate image.

Referring to FIG. 9, a master substrate image (MSI) is subtracted from the substrate image (ISI) to form a comparison image (PI). The master substrate image (MSI) is a clean image without a foreign substance. Therefore, when the substrate image (ISI) contains a foreign substance (FM), there exists only the foreign substance (FM) in the comparison image (PI).

On the other hand, in order to enhance detection performance of the foreign substance (FM) in the comparison image (PI), the comparison (PI) may be binary-coded based on a specific reference value to form a binary-coded image (BI). In the binary-coded image (BI), a foreign substance (FM) region and other regions are clearly distinguished. Therefore, detecting a foreign substance is enhanced. Additionally, when a noise removing is performed regarding to the binary-coded image (BI), detecting a foreign substance is further enhanced.

Referring again to FIG. 7, a dark foreign substance such as a hair, an insulation tape, etc. is detected by using the master images per color and the obtained images per color, after detecting the bright foreign substance (S240).

Figure 10:
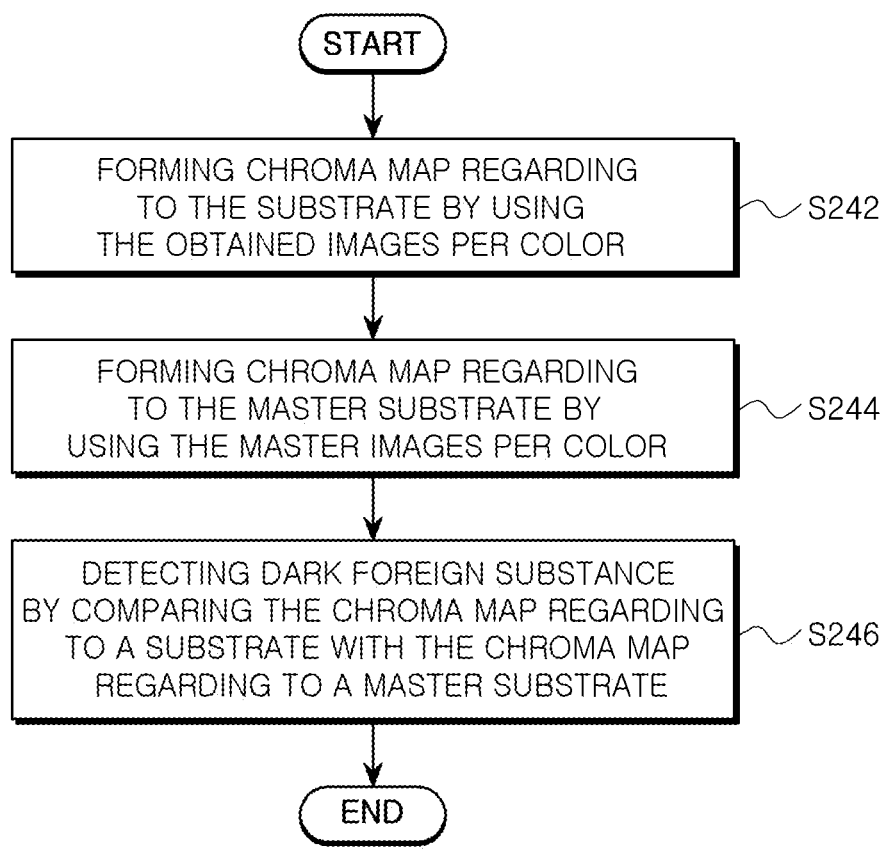
FIG. 10 is a flow chart showing a process of detecting a dark foreign substrate.

FIG. 10 is a flow chart showing a process of detecting a dark foreign substrate.

Referring to FIG. 10, a chroma (or saturation) map regarding the substrate 10 is formed by using the obtained images per color (S242).

Additionally, a chroma map regarding to the master substrate is formed by using the master images per color (S244).

For example, the chroma map may be formed by using chroma information of a red image, a green image and a blue image per pixel. In detail, the chroma map may be formed based on chroma per pixel, which is calculated by the following Equation 1.

$$\text{Saturation} = (1 - 3 * \text{Min}(R,G,B)/(R+G+B))$$   Equation 1

In the Equation 1, 'R' is a chroma information of each pixel in the red image, 'G' is a chroma information of each pixel in the green image, and 'B' is a chroma information of each pixel in the blue image.

The chroma map 300 obtained by using the Equation 1 has a value 0~1 per pixel, and a value means a primary color, when the value approaches to 1. In general, a dark foreign substance is near to achromatic color, so that the dark foreign substance region is expressed as a region with a value near to 0.

After forming the chroma map regarding to a substrate and the chroma map regarding to a master substrate through the Equation 1, a dark foreign substance is detected by comparing the chroma map regarding to a substrate with the chroma map regarding to a master substrate (S246).

Figure 11:
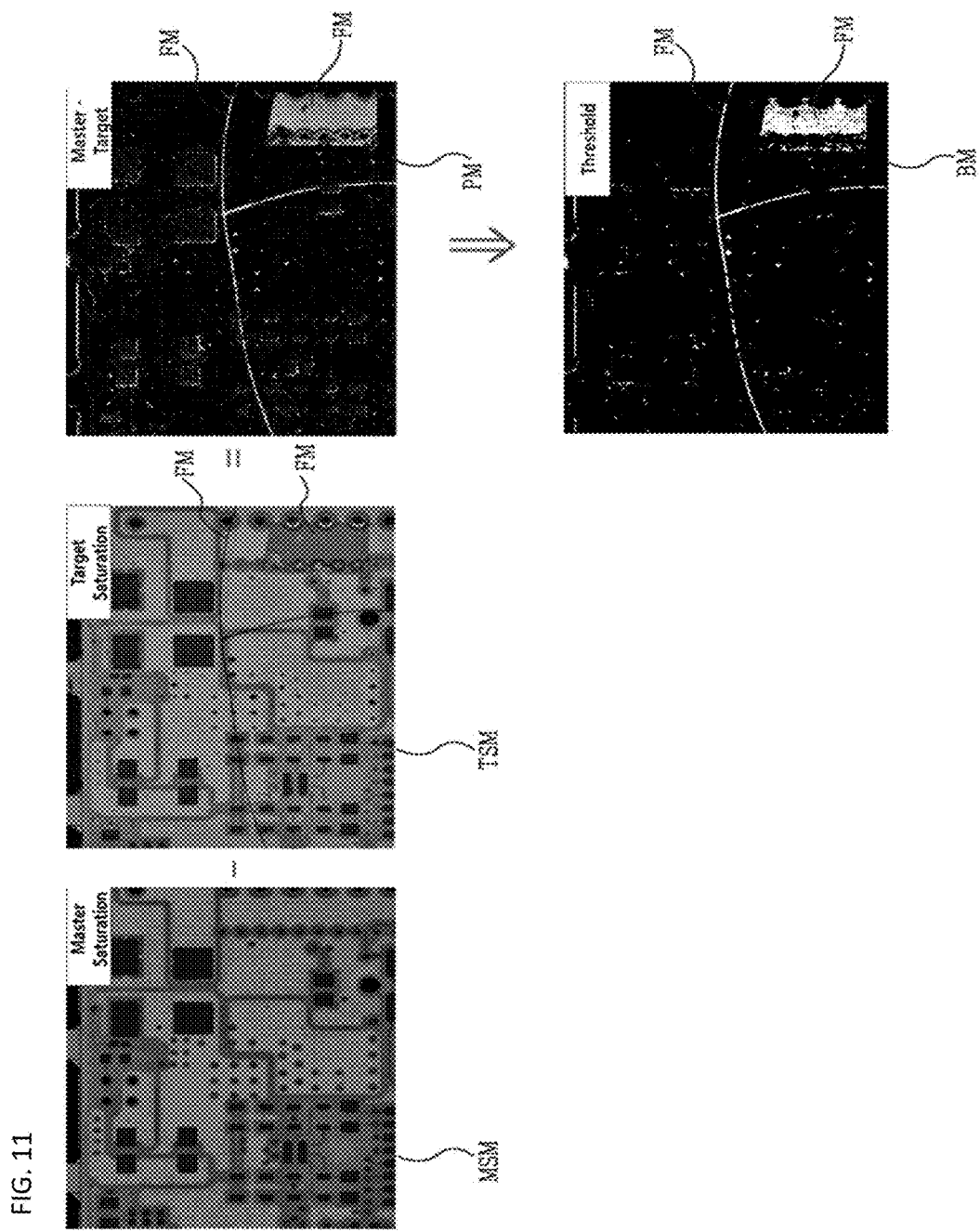
FIG. 11 is a conceptual view showing a process of detecting a dark foreign substance by comparing a chroma map of a substrate and a chroma map of a master substrate.

FIG. 11 is a conceptual view showing a process of detecting a dark foreign substance by comparing a chroma map of a substrate and a chroma map of a master substrate.

Referring to FIG. 11, a chroma map (TSM) regarding to a substrate is subtracted from a chroma map (MSM) regarding to a master substrate to form a comparison image (PM). When there exists a foreign substance (FM) in the chroma map (TSM) of the substrate, the foreign substance (FM) can be seen in the comparison image (PM).

On the other hand, in order to enhance detection performance of the foreign substance (FM) in the comparison image (PM), the comparison (PM) may be binary-coded based on a specific reference value to form a binary-coded image (BM). In the binary-coded image (BM), a foreign substance (FM) region and other regions are clearly distinguished. Therefore, detecting a foreign substance (FM) is enhanced.

Further, after a foreign substance (FM) region is firstly identified by using the binary-coded image (BM), the region with the foreign substance (FM) is set as a region of interest (ROI), and color analysis may be performed regarding to the region of interest (ROI) to perform more precise detection. For example, after chroma map of the whole substrate is compared and analyzed, a region with a foreign substance (FM) is set as the region of interest (ROI). Then, other regions are mask-processed to be excluded, and the region of interest (ROI) is selectively amplified to generate region of interest (ROI) image by merging color images (for example, a red image, a green image and a blue image) of the region of interest (ROI). Then, binary-coding and noise-removing are performed regarding to the region of interest, so that a foreign substance can be more precisely detected.

Referring again to FIG. 7, a detection result of the bright foreign substance and a detection result of the dark foreign substance are merged (S250). That is, the detection results of a bright foreign substance and the dark foreign substance are merged to finally detect foreign substances of the substrate.

As described above, when a bright foreign substance and a dark foreign substance are separately detected and merged in inspecting of a foreign substance of a substrate, a reliability of detection of a foreign substance can be improved.

On the other hand, when a foreign substance is estimated if it is bright or dark, or detection of only one of a dark foreign substance and a bright foreign substance is required, only the detection of only one of a dark foreign substance and a bright foreign substance may be employed.

Alternatively, when a foreign substance cannot be estimated if it is bright or dark, or detection of both of a dark foreign substance and a bright foreign substance is required, detection of both of a dark foreign substance and a bright foreign substance may be performed and the sequence of detection of a dark foreign substance and detection of a bright foreign substance is not limited.

On the other hand, a foreign substance exclusively corresponds to a bright foreign substance or a dark foreign substance. Therefore, when a substance is considered a bright foreign substance or a dark foreign substance, the substance is considered as a foreign substance.

Figure 12:
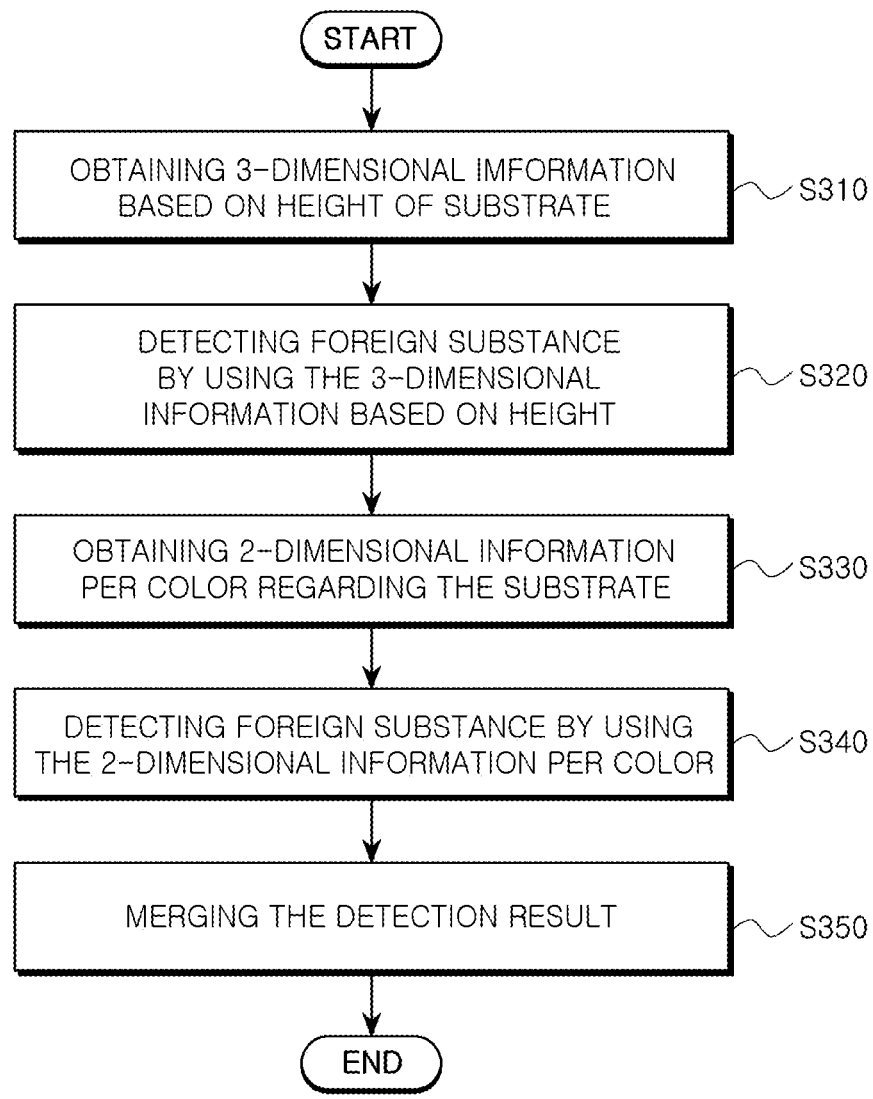
FIG. 12 is a flow chart showing a method of inspecting a foreign substance according to still another embodiment of the present invention.

FIG. 12 is a flow chart showing a method of inspecting a foreign substance according to still another embodiment of the present invention.

Referring to FIG. 12, in order to inspect a foreign substance according to still another embodiment of the present invention, a 3-dimensional information based on height of a substrate is obtained by using at least grid pattern light (S310). That is, 3-dimensional information including height information of a substrate is obtained by using at least one of the projection parts 300 and 400.

Then, a foreign substance of the substrate is detected by using the 3-dimensional information based on height (S320).

For example, a region of abrupt height change or a region exceeding a previously set reference height may be considered as a foreign substance in the 3-dimensional information based on height of the substrate to detect a foreign substance.

Aside from detecting a foreign substance by using the 3-dimensional information, 2-dimensional information per color is obtained by using a plurality of color light (S330).

Then, a foreign substance of the substrate is detected by using the 2-dimensional information per color (S340). The method of detecting foreign substance by using the 2-dimension information is substantially same as the embodiment explained referring to FIG. 7 through FIG. 11. Therefore, any further explained will be omitted.

Then, a detection result obtained by using the 3-dimensional information based on height and a detection result obtained by using 2-dimensional information per color are merged (S350). That is, the detection result obtained by using the 3-dimensional information based on height and the detection result obtained by using 2-dimensional information per color are merged to detect finally a foreign substance.

As described above, when the detection result obtained by using the 3-dimensional information based on height and the detection result obtained by using 2-dimensional information per color are merged, a reliability of detection of a foreign substance can be improved in detecting a foreign substance of a substrate.

On the other hand, in order for exact detection or minimum error, a substance may be considered as a foreign substance when the substance is considered as a foreign substance in both of the detection by using the 3-dimensional information based on height and the detection by using the 2-dimensional information per color.

Alternatively, a substance may be considered as a foreign substance when the substance is considered as a foreign substance in one of the detection by using the 3-dimensional information based on height and the detection by using the 2-dimensional information per color.

On the other hand, a region which may be wrongly considered as a foreign substance or a region necessary to be removed may be removed before detecting a foreign substance by using the 3-dimensional information based on height and detecting a foreign substance by using the 2-dimensional information per color.

Figure 13:
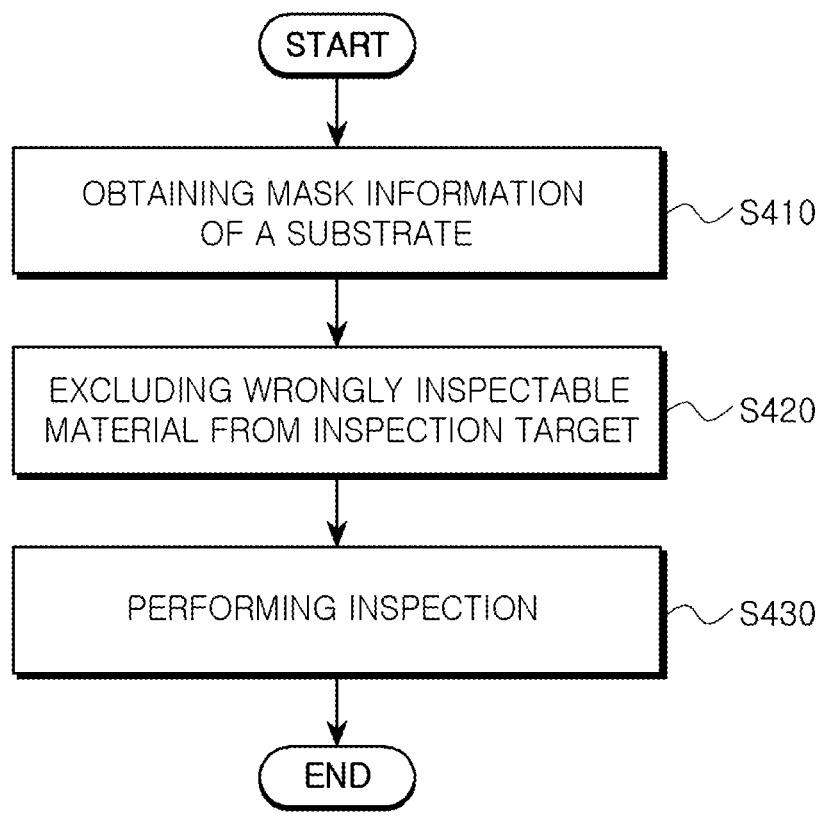
FIG. 13 is a flow chart showing a method of inspecting a foreign substance according to still another embodiment of the present invention.

FIG. 13 is a flow chart showing a method of inspecting a foreign substance according to still another embodiment of the present invention.

Referring to FIG. 13, in order to inspect a foreign substance of a substrate according to still another embodiment of the present invention, a mask information of the substrate is firstly obtained (S410).

For example, the mask information may include a hole information formed at the substrate. A hole formed at the substrate may be different from a hole formed at the master substrate in size, so that a hole may be wrongly considered as a foreign substance, when a hole is included in an inspection target that is to be detected. Therefore, in order to eliminate the possibility of wrong inspection, a hole may be removed from an inspection target that is to be detected. In this case, the mask information such as a hole information may be obtained by using an infrared (IR) lighting.

For example, the mask information may include a circuit pattern information formed on the substrate. The circuit pattern is generally formed through an etching process, and a circuit pattern formed on a substrate may be different from a circuit pattern formed on the master substrate in position, so that a circuit pattern may be wrongly considered as a foreign substance, when the circuit pattern is included in an inspection target that is to be detected. Therefore, in order to eliminate the possibility of wrong inspection, a circuit pattern may be removed from an inspection target that is to be detected.

The mask information regarding a substrate may be obtained from the substrate or the master substrate.

Then, a mask is generated based on the mask information to remove wrongly inspectable material from inspection target (S420).

For example, a hole mask including a hole of the substrate, and an edge mask including a circuit pattern of the substrate may be formed. The hole mask and the edge mask can exclude a hole and a circuit pattern from an inspection target to be detected.

After excluding wrongly inspectable material from the inspection target to be detected, a foreign substance may be inspected based on the 3-dimensional information based on height and the 2-dimensional information per color (S430).

As described above, more easy or precise detection can be performed by excluding a region that is unnecessary or may induce error in inspecting a foreign substance by using infrared lighting.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents. Therefore, the above explanation and following figures may be understood not to limits the idea of the present invention but to be examples.

The invention claimed is:

1. A method of inspecting a foreign substance on a substrate, the method comprising:

obtaining 3-dimensional information based on height of a substrate by using at least one grid pattern light;

detecting a foreign substance of the substrate by using the 3-dimensional information based on height;

obtaining 2-dimensional information of the substrate per color by using a plurality of color light;

detecting a foreign substance of the substrate by using the 2-dimensional information per color; and merging a detection result of a foreign substance, performed by using the 3-dimensional information based on height and a detection result of a foreign substance, performed by using the 2-dimensional information per color, wherein detecting a foreign substance of the substrate by using the 2-dimensional information per color, comprises:

obtaining master images of a master substrate per color by using the plurality of color light;

obtaining images of the substrate per color by using the plurality of color light; and comparing the master images per color and the images per color to detect a foreign substance.

2. The method claim 1, wherein comparing the master images per color and the images per color to detect a foreign substance, comprises:
- merging the images of the substrate per color to generate a substrate image;
- merging the master images of the master substrate per color to generate a master substrate image; and
- comparing difference of the substrate image and the master substrate image to detect a foreign substance.

3. The method claim 1, wherein comparing the master images per color and the images per color to detect a foreign substance, comprises:
- forming a chroma map of the substrate by using the images of the substrate per color;
- forming a chroma map of the master substrate by using the master images of the master substrate per color; and
- comparing the chroma map of the substrate and the chroma map of the master substrate to detect a foreign substance.

4. The method of claim 1, wherein merging a detection result of a foreign substance, performed by using the 3-dimensional information based on height and a detection result of a foreign substance, performed by using the 2-dimensional information per color, comprises:
- determining a foreign substance as a final foreign substance, when the foreign substance is considered as a foreign substance in both of inspection by using the 3-dimensional information based on height and inspection by using the 2-dimensional information per color.

5. The method of claim 1, before detecting a foreign substance of the substrate by using the 3-dimensional information based on height and detecting a foreign substance of the substrate by using the 2-dimensional information per color, further comprising:
- obtaining a mask information regarding to the substrate by using a infrared lighting; and
- excluding wrongly inspectable material from an inspection target to be detected by forming a mask based on the mask information.

6. The method of claim 5, wherein the mask information comprises a hole information formed at the substrate.

7. A method of inspecting a foreign substance on a substrate, the method comprising:
- obtaining master images of a master substrate per color by using a plurality of color light;
- obtaining images of a substrate per color by using the plurality of color light;
- forming a master substrate image by merging the master images of the master substrate per color and a substrate image by merging the images of the substrate per color;
- detecting a first foreign substance by comparing the substrate image and the master substrate image;
- forming a chroma map of the master substrate by using the master images of the master substrate per color and a chroma map of the substrate by using the images of the substrate per color;
- detecting a second foreign substance by comparing the chroma map of the substrate and the chroma map of the master substrate; and
- merging a detection result of the first foreign substance and a detection result of the second foreign substance.

8. The method of claim 7, wherein merging a detection result of the first foreign substance and a detection result of the second foreign substance, comprises:
- determining a foreign substance as a final foreign substance, when the foreign substance is considered as a foreign substance in at least one of a detection result of the first foreign substance and a detection result of the second foreign substance.

9. The method of claim 7, before detecting a first foreign substance and a second foreign substance, further comprising:
- obtaining a mask information regarding the substrate; and
- excluding wrongly inspectable material from an inspection target to be detected by forming a mask based on the mask information.

10. The method of claim 9, wherein excluding wrongly inspectable material from an inspection target to be detected by forming a mask based on the mask information, comprises:
- forming a hole mask such that a hole formed at the substrate is included;
- forming an edge mask such that a circuit pattern formed on the substrate is included; and
- excluding the hole mask and the edge mask from the inspection target to be detected.

11. The method of claim 7, further comprising:
- obtaining 3-dimensional information based on height of a substrate by using at least one grid pattern light;
- detecting a foreign substance of the substrate by using the 3-dimensional information based on height; and
- merging a detection result based on the 3-dimensional information based on height and a detection result based on 2-dimensional information of color, after detecting a foreign substance of the substrate by using the 3-dimensional information based on height and merging a detection result of the first foreign substance and a detection result of the second foreign substance.

12. The method of claim 11, wherein merging a detection result based on the 3-dimensional information based on height and a detection result based on 2-dimensional information of color, comprises:
- determining a foreign substance as a final foreign substance, when the foreign substance is considered as a foreign substance in both of the detection result based on the 3-dimensional information based on height and the detection result based on 2-dimensional information of color.

* * * * *